United States Patent
Makarov

(10) Patent No.: US 7,138,556 B2
(45) Date of Patent: Nov. 21, 2006

(54) METHOD FOR PRODUCING AROMATIC HYDROCARBONS

(76) Inventor: Pavel A Makarov, kv. 308, d. 9, pr Vernadskogo, Moscow (RU) 117311

( * ) Notice: Subject to any disclaimer, the term of this patent is extended or adjusted under 35 U.S.C. 154(b) by 315 days.

(21) Appl. No.: 10/363,458

(22) PCT Filed: Jul. 25, 2002

(86) PCT No.: PCT/RU02/00356

§ 371 (c)(1),
(2), (4) Date: Feb. 26, 2004

(87) PCT Pub. No.: WO03/091362

PCT Pub. Date: Nov. 6, 2003

(65) Prior Publication Data

US 2004/0143148 A1    Jul. 22, 2004

(30) Foreign Application Priority Data

Apr. 25, 2002  (RU) .............................. 2002111023

(51) Int. Cl.
*C07C 2/76*   (2006.01)

(52) U.S. Cl. ...................................... 585/418; 585/906

(58) Field of Classification Search ................ 585/418, 585/906
See application file for complete search history.

(56) References Cited

U.S. PATENT DOCUMENTS 2,863,825 A    12/1958   Engel

FOREIGN PATENT DOCUMENTS

RU   2030376   3/1995
RU   2163624   2/2001

*Primary Examiner*—Thuan Dinh Dang
(74) *Attorney, Agent, or Firm*—patenttm.us; James H. Walters

(57) ABSTRACT

The method comprises separation of contacting products into liquid and gaseous products, complete burning of gaseous products in the presence of the catalyst of complete oxidation of light hydrocarbons and addition of carbon dioxide and water vapor mixture formed during burning to the raw paraffin hydrocarbons. The mixture of paraffin hydrocarbons $C_2 \div C_5$ is used as a raw material in this method. Before feeding the said mixture of hydrocarbons the catalyst is subjected to treatment by paraffin hydrocarbons $C_3 \div C_4$ mixed with mercaptan so that the amount of mercaptan passed through the catalyst is 0.01–0.1 mass % of the catalyst weight.

2 Claims, No Drawings

METHOD FOR PRODUCING AROMATIC HYDROCARBONS

FIELD OF ART

The invention relates to the field of chemistry, namely, to the methods for producing aromatic hydrocarbons from light hydrocarbons, including casing-head gas from the end stages of separation.

PRIOR ART

There is a known method for processing light hydrocarbons in the presence of high-silica zeolite. The method consists in passing a mixture of hydrocarbons containing $C_1 \div C_{10}$, for example, light naphtha through a high-silica ceolite-based catalyst with additions of Cu, Zn or Cr at $300 \div 700°$ C. (JP, A, No. 59-152337).

A limitation of the known method is formation of carbon compound deposits (coke deposits) on the catalyst, which considerably impairs its activity.

There is a known method for producing aromatic hydrocarbons by means of contacting paraffin hydrocarbons $C_3 \div C_{11}$ with ZSM-type high-silica zeolite-based catalyst at $380 \div 580°$ C., which comprises separation of contacting products into liquid and gaseous products (DE, A, No. 251710).

The process takes place on the catalyst comprising ZSM-5 type zeolite ($SiO_2/Al_2O_3$ 20–100) and metals of group II (Zn) separately or in combination with metals of group VI (Cr) and/or group II (Cu) in the amount of $0.01 \div 5\%$ in terms of metal.

A limitation of this method is a low yield of the target product as well as a high extent of the catalyst clogging with coke and a short duration of the operating cycle of the process.

The closest to this invention is the method for producing aromatic hydrocarbons (RU, A, No. 2030376).

In the known method, which comprises contacting paraffin hydrocarbons $C_3 \div C_{11}$ with ZSM-5 type high silica zeolite-based catalyst at $380 \div 580°$ C., separation of the contacting products into liquid and gaseous products, the gaseous products are subjected to complete burning in the presence of the catalyst of complete oxidation of light hydrocarbons, and the mixture of carbon dioxide and water vapor formed during burning is added to the raw paraffin hydrocarbons in the amount of $2.0 \div 20.0\%$.

The known method affords the improvement of technical-and-economic indices of the process of converting light hydrocarbons into aromatic hydrocarbons through increasing a length of the catalyst service cycle (increasing the catalyst stable activity). Nevertheless the duration of the service cycle in the known method determined by a period of catalyst stable activity is insufficient.

DISCLOSURE OF THE INVENTION

The basis for this invention is the task of creating the method for producing aromatic hydrocarbons, which provides the increase of the catalyst stable activity period, and thereby a long duration of the service cycle is achieved.

The above-said technical effect is achieved by using the method for producing aromatic hydrocarbons through contacting paraffin hydrocarbons with ZSM-5 type high-silica zeolite-based catalyst at $400 \div 550°$ C., which comprises separation of the contacting products into liquid and gaseous products, complete burning of the gaseous products in the presence of the catalyst of complete oxidation of light hydrocarbons and adding the mixture of carbon dioxide and water vapor formed during their burning to the raw paraffin hydrocarbons, according to the invention the mixture of $C_2 \div C_5$ is used as paraffin hydrocarbons. Before feeding said mixture of hydrocarbons the catalyst is subjected to treatment by paraffin hydrocarbons $C_3 \div C_4$ mixed with mercaptan so that the amount of mercaptan passed through the catalyst makes up $0.01 \div 0.1$ mass % of the catalyst weight.

An additional embodiment of the method is possible wherein it is desirable to maintain the content of mercaptan mixed with paraffin hydrocarbons $C_3 \div -C_4$ in the range from 0.08 to 0.85 mass %, respectively, and to perform the catalyst treatment at temperatures between 450 and $520°$ C.

The above-mentioned advantages and the attributes of this invention are explained by way of its best embodiments.

THE BEST EMBODIMENTS OF THE INVENTION

An essence of this invention is illustrated by way of the following examples.

Examples 1, 2, 3, 4 show the results of the method realization with adding the mixture of carbon dioxide and water vapor to light hydrocarbons (the ratio between the amount of carbon dioxide and water being 20:1). The amount of the added gases varied and made up 2.0; 5.0; 12.0 and 20.0 mass % of the amount of the raw hydrocarbons fed to the reactor.

EXAMPLE 1

In the process of producing aromatic hydrocarbons there was used a catalyst comprising 57.0% of ZSM-5 high-silica zeolite with the following ratio of ingredients: 39 mass % $SiO_2/Al_2O_3$; 36.4 mass % $Al_2O_3$; 3.5 mass % $B_2O_3$; 3.0 mass % Zn.

4 kg of catalyst were placed into a steel reactor of the unit and heated up in the stream of the heated air with a flow of 80 l/h to a temperature of $500°$ C. Thereafter the catalyst was blown by nitrogen with a flow of 80 l/h for 2 hours at a specified temperature. Then nitrogen supply was stopped, and the mixture of raw materials, light hydrocarbons $C_2 \div C_5$, was fed into the reactor.

The mixture of light hydrocarbons $C_2 \div C_5$ with the following composition: 9.0 mass % $C_2$; 25.0 mass % $C_3$; 62.0 mass % $C_4$; 4.0 mass % $C_5$ was used as raw material. The process was conducted at a temperature of $510°$ C., a volume velocity of 320 $h^{-1}$ in terms of the gaseous raw materials.

The gaseous reaction products were burned to complete oxidation in the presence of the catalyst of complete oxidation (vanadium catalysts $V_2O_5/MoO_3$ in form of granules were used as a catalyst of complete oxidation). Gaseous by-products at a temperature of $550°$ C. and at a volume velocity of 250 $h^{-1}$ were subjected to complete oxidation (the weight of the catalyst of complete oxidation was 800 g) up to formation of carbon dioxide and water vapor.

Under these conditions the yield of aromatic hydrocarbons ($C_6 \div C_9$) made up 61.4%; the yield of aliphatic hydrocarbons made up 0.1%, that of gases made up 28.0% (including 2.5% hydrogen, 4.0% methane, 7.5% $C_2$, 19% $C_3 \div C_4$, 0.5% coke).

The catalyst retains stable activity in the reaction of light hydrocarbon conversion during 260 hours. The evaluation of the catalyst stability was carried out in terms of the yield of aromatic hydrocarbons. A drop in the yield of aromatic hydrocarbons by 30% was used as a criterion of loss in stability.

In examples 2, 3, 4 the conditions of the method realization were similar to example 1, except that the amount of carbon dioxide and water vapor added to raw material were 2–5 mass % in example 2; 3–12 mass % in example 3 and 4–20 mass % in example 4.

The results are shown in Table 1.

TABLE 1

| Number of example | Amount of carbon dioxide and water mixture added during reaction, mass % | Increase in duration of catalyst stable operation, % |
|---|---|---|
| 1 | 2.0 | no |
| 2 | 5.0 | 2.0 |
| 3 | 12.0 | 10.5 |
| 4 | 20.0 | no |

The stage of catalyst preliminary treatment by paraffin hydrocarbons $C_3 \div C_4$ mixed with mercaptan at a temperature from 450 to 520° C. has been introduced for increasing the period of catalyst stable operation. The amount of added mercaptan varied from 0.01 to 0.1 mass % of the catalyst weight.

The results of the method realization with preliminary treatment of catalyst by mixture of paraffin hydrocarbons $C_3 \div C_4$ with additions of mercaptan are shown in Table 2. In these experiments after catalyst treatment by paraffin hydrocarbons $C_3 \div C_4$ with mercaptan additions the raw material was fed into the reactor—light hydrocarbons $C_2 \div C_5$ with addition of 12 mass % carbon dioxide and water vapor (of the raw material weight).

EXAMPLE 5

In the process of producing aromatic hydrocarbons there was used a catalyst comprising 57.1 mass % ZSM-5 high-silica zeolite with the following ratio of ingredients: 39 mass % $SiO_2/Al_2O_3$; 36.4 mass % $Al_2O_3$; 3.5 mass % $B_2O_3$; 3.0 mass % Zn. 4 kg of catalyst were placed into the steel reactor of the unit and heated up in the stream of the heated air with a flow of 80 l/h to a temperature of 500° C. Thereafter the catalyst was blown by nitrogen with a flow of 80 l/h for 2 hours at a specified temperature. Then nitrogen supply was stopped, and the mixture of paraffin hydrocarbons $C_3 \div C_4$ was supplied into the reactor with mercaptan additions so that 0.01 weight % mercaptan was passed through the catalyst. Thereafter the gas mixture supply was stopped, and the raw material—the mixture of light hydrocarbons $C_2 \div C_5$ with the following composition: 9.0 mass % $C_2$; 25.0 mass % $C_3$; 62.0 mass % $C_4$; 4.0 mass % $C_5$ was fed into the reactor with addition of 12 mass % carbon dioxide and water vapor mixture of the raw material weight.

Examples 5, 6, 7, 8, 9 differ only in the amount of mercaptan passed through the catalyst. In these examples mercaptan concentration of the mixture of paraffin hydrocarbons $C_3 \div C_4$ during preliminary catalyst treatment was 0.3–0.4 mass %.

TABLE 2

| Number of example | Amount of mercaptan fed through the catalyst, mass % | Increase in duration of catalyst stable operation, % |
|---|---|---|
| 5 | 0.01 | no |
| 6 | 0.05 | 2.0 |
| 7 | 0.08 | 8.0 |
| 8 | 0.1 | 4.0 |
| 9 | 0.15 | no |

In the examples the ratio between paraffin hydrocarbons $C_3 \div C_5$ and mercaptan in the mixture is 0.76 mass %.

The conditions of the method realization in examples 10, 11, 12 were similar to those in example 7, except that with the total amount of mercaptan fed through the catalyst being kept at the same level, its concentration in mixture of paraffin hydrocarbons $C_3 \div C_4$ used for catalyst preliminary treatment were varied. It was achieved through dilution of the specified amount of mercaptan by different volumes of paraffin $C_3 \div C_4$.

EXAMPLE 9

In the process of producing aromatic hydrocarbons there was used a catalyst comprising 57.0% of ZSM-5 high-silica zeolite with the following ratio of its ingredients: 39 mass % $SiO_2/Al_2O_3$; 36.4 mass % $Al_2O_3$; 3.5 mass % $B_2O_3$; 3.0 mass % Zb. 4 kg of the catalyst were placed into the steel reactor of the unit and heated up in the stream of the heated air with a flow of 80 l/h to a temperature of 500° C. Thereafter the catalyst was blown by nitrogen with a flow of 80 l/h for 2 hours at a specified temperature. Then nitrogen supply was stopped, and the mixture of paraffin hydrocarbons $C_3 \div C_4$ with mercaptan additions was fed into the reactor so as 0.08 mass % mercaptan to the catalyst mass to be passed through the catalyst. In this case a volume of paraffin $C_3 \div C_4$ passed through the catalyst made up 1600 l, and the mercaptan concentration of them was 0.08 mass %. Thereafter the supply of gas mixture was stopped, and there was fed into the reactor the raw material, the mixture of light hydrocarbons $C_2 \div C_5$ with the following composition: 9.0 mass % $C_2$; 25.0 mass % $C_3$; 62.0 mass % $C_4$; 4.0 mass % $C_5$, with addition of 12 mass % carbon dioxide and water vapor mixture of the weight of the raw material. Under these conditions the increase in the duration of the catalyst stable operation made up 4.4%.

EXAMPLE 10

The process conditions are similar to those in example 9, except that the volume of the mixture of paraffin hydrocarbons $C_3 \div C_4$ was 400 l, and the mercaptan concentration of them was 0.32 mass %. The increase in the duration of the catalyst stable operation made up 8.0%.

EXAMPLE 11

The process conditions are similar to those in example 9, except that the amount of paraffin hydrocarbons $C_3 \div C_4$ passed through the catalyst was 200 l, and the mercaptan concentration of them made up 0.65 mass %. In this case the increase in the duration of the catalyst stable operation made up 2.4%.

INDUSTRIAL APPLICABILITY

The applied method for producing aromatic hydrocarbons can be used most successfully for producing aromatic hydrocarbons from light hydrocarbons, including the casing-head gas of the end stages of separation.

The invention claimed is:

1. A method for producing aromatic hydrocarbons comprising:
    contacting paraffin hydrocarbons with a ZSM-5 type high-silica zeolite-based catalyst at a temperature from 400 to 550° C.,
    separating the contacting products into liquid and gaseous products,
    complete burning of gaseous products in the presence of a catalyst of complete oxidation of light hydrocarbons and
    adding carbon dioxide and water vapor mixture formed during burning to the raw paraffin hydrocarbons,
    wherein a mixture of paraffin hydrocarbons $C_2 \div C_5$ is used as raw material, and
    before feeding the said mixture of hydrocarbons,
    subjecting the catalyst to treatment by paraffin hydrocarbons $C_3 \div C_4$ mixed with mercaptan so that the amount of mercaptan passed through the catalyst is 0.01–0.1 mass % of the catalyst weight.

2. A method for producing aromatic hydrocarbons comprising:
    contacting paraffin hydrocarbons with a ZSM-5 type high-silica zeolite-based catalyst at a temperature from 450 to 520° C.,
    separating the contacting products into liquid and gaseous products,
    complete burning of gaseous products in the presence of a catalyst of complete oxidation of light hydrocarbons and
    adding carbon dioxide and water vapor mixture formed during burning to the raw paraffin hydrocarbons,
    wherein a mixture of paraffin hydrocarbons $C_2 \div C_5$ is used as raw material, and
    before feeding the said mixture of hydrocarbons,
    subjecting the catalyst to treatment by paraffin hydrocarbons $C_3 \div C_4$ mixed with mercaptan so that the amount of mercaptan passed through the catalyst is 0.08–0.85 mass % of the catalyst weight.

* * * * *